Figure 1:
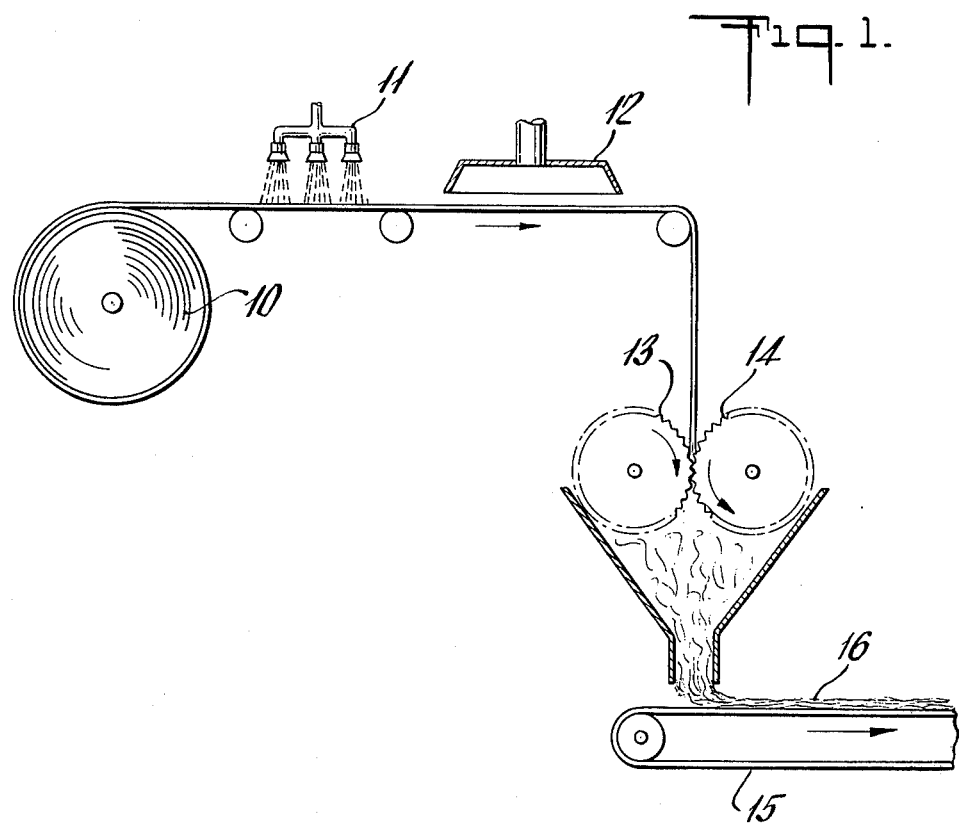

United States Patent [19]

Levesque

[11] 4,022,861
[45] * May 10, 1977

[54] METHODS OF MANUFACTURING WATER-REPELLENT FLUFFY BATTS OF WOOD PULP FIBERS

[75] Inventor: Yvon George Levesque, Montreal, Canada

[73] Assignee: Johnson & Johnson, New Brunswick, N.J.

[*] Notice: The portion of the term of this patent subsequent to Apr. 13, 1993, has been disclaimed.

[22] Filed: June 10, 1975

[21] Appl. No.: 585,438

Related U.S. Application Data

[63] Continuation-in-part of Ser. No. 431,193, Jan. 7, 1974, abandoned.

[52] U.S. Cl. .............................. 264/116; 162/100; 162/183; 162/213; 264/91; 264/121
[51] Int. Cl.² .......................................... D04H 3/16
[58] Field of Search .......... 162/100, 182, 184, 183, 162/213; 241/28; 264/121, 116, 118, 128, 91; 128/284, 287

[56] References Cited

UNITED STATES PATENTS

| 3,554,863 | 1/1971 | Hervey et al. | 162/158 |
| 3,677,886 | 7/1972 | Forssblad et al. | 162/182 |
| 3,756,913 | 9/1973 | Wodka | 162/100 |

OTHER PUBLICATIONS

Casey, "Pulp & Paper", vol. II (1960), 2nd ed., p. 947.

Primary Examiner—S. Leon Bashore
Assistant Examiner—Peter Chin

[57] ABSTRACT

A method of manufacturing a water-repellent, fluffy lightweight batt of wood pulp fibers comprising applying a water-repellent material to a surface of a dry wood pulp board so that the water-repellent penetrates through only a portion of the board. The treated board is ground to individualize the fibers, and the ground fibers are collected in a batt with the water-repellent treated fibers distributed uniformly throughout to produce a fluffy, water-repellent batt of wood pulp fibers.

3 Claims, 2 Drawing Figures

U.S. Patent   May 10, 1977   4,022,861

METHODS OF MANUFACTURING WATER-REPELLENT FLUFFY BATTS OF WOOD PULP FIBERS

This application is a continuation-in-part of application Ser. No. 431,193, filed January 7, 1974 now abandoned.

This invention relates to a water-repellent, fluffy, lightweight batt of wood pulp fibers, and to methods of manufacturing the same.

In many absorbent products such as diapers, sanitary napkins, dressings and the like it has been desired to have one surface of the absorbent product water repellent either to hold the liquid being absorbed by the product or to maintain that surface dry. A number of techniques have been developed for accomplishing these purposes such as by placing on one surface of the absorbent media a thermoplastic water-repellent film or by spraying one surface with a water repellent film or by spraying one surface with a water repellent material. In these prior art techniques the characteristics of hand, softness, loft and so on of the water-repellent surface is changed and hence such surfaces do not have the desired feel of the absorbent media itself.

In accordance with the present invention I have now discovered a very soft, lofty, liquid barrier of wood pulp fibers. My new product may be used by itself or in combination with absorbent materials and the like and my new product has substantially the same feel and hand as the absorbent media itself.

Furthermore, unlike a thin water-repellent layer which tends to wet easily, my fluffy layer must be compressed before it tends to wet making our new layer especially useful as the facing member of a disposable diaper.

In accordance with the present invention our soft, lofty liquid barrier comprises a batt of wood pulp fibers having a density of from about 0.03 to 0.30 grams per cubic centimeter and having uniformly distributed throughout the batt a water-repellent material comprising from about ¼% to 2% by weight of the batt. At least 45% of the wood pulp fibers are treated with the water-repellent material.

My new soft, lofty, liquid barrier is made by treating a surface of wood pulp board with a water-repellent material. The board is treated from about 45 to 95% of its thickness so as to leave some completely untreated wood pulp fibers in the board. The treated board is ground to comminute the board and individualize the fibers. The individualized fibers have varying amounts of water repellent on their surface with a portion of the fibers having no water repellent and are collected as a batt of wood pulp fibers with the water repellent material substantially uniformly distributed throughout the thickness of the batt. The resulting batt is water repellent, has an excellent hand, is very soft and has good loft. The batt may be used by placing on its top surface untreated wood pulp fibers which have high absorbative capacity and this laminate wrapped in a nonwoven fabric to produce the final absorbent product. The water-repellent batt may be used with crepe tissue or other material which will provide the desired absorbency in the final product or it could be used by itself in those end uses where absorbency rate is unimportant but some absorbent capacity may be desired.

Figure 2:
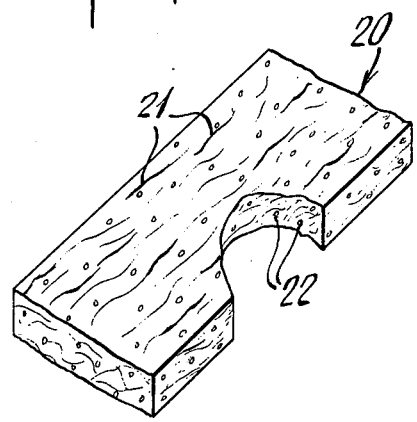

The invention is more readily understood by reference to the accompanying drawings wherein:

FIG. 1 is a schematic drawing of one form of apparatus for carrying out the method of the present invention and FIG. 2 is a perspective view of a fluffy water-repellent wood pulp batt of the present invention.

Referring to FIG. 1 of the drawings a supply of wood pulp board 10 in compacted sheet form is fed from a roll to a spraying station 11. This wood pulp board is the pressed sheet of pulp which is prepared by pulp mills, and is rolled into a large supply roll. The wood pulp board 10 in rolled sheet form is hard due to the tightly pressed pulp fibers within the board, and is substantially dry, containing only the inherent moisture that accompanies the fibers after the pressing oreration at the pulp mills. This board does not go through the water box or aqueous beater stage as is known in the art, to the spraying station, but is fed in the dry, non-aqueous condition.

A water-repellent material is sprayed onto the surface of the board. The water-repellent is sprayed onto the surface of the board in its dry state so that it only penetrates through a portion of the depth of the board and a portion of the board is left untreated with water repellent. The treated portion of the wood pulp board lies within the range of 45 to 95% of treated fibers. There is a wide range of treated fibers due to the density of the board being used, the differing viscosities of the water-repellent material being applied and the method of application of water-repellent material to the board, whether spraying, coating, depositing, printing or the like. The criticality of the application of water-repellent lies in leaving some of the fibers completely untreated in the wood pulp board. As the water-repellent material is applied there may be some fibers which receive more water-repellent than others, i.e., the fibers are not uniformly or consistently treated. This lack of uniformity of treatment of fibers is acceptable and presents no problems in the formation of the water-repellent batt. The critical feature of having some fibers untreated is essential to provide softness, fluffiness, loft and good hand and feel to the final batt. But yet, while only a portion of the fibers are treated with a water-repellent, the final formed batt, as hereinafter described, is entirely water-repellent. Thus, by the combination of treated and untreated fibers in the manufacturing of a batt no compromise has to be made between a batt with good soft, lofty, fluffy properties and total water-repellency.

The treated board passes through an oven 12 to dry the board and remove whatever carrier has been used for applying the water-repellent material. The treated pulp board passes through a grinding apparatus which in this instance comprises a pair of counter-rotating toothed rolls 13 and 14 which comminute the pulp board and individualize the fibers. The individual fibers, some of which are uncoated and others having varying amounts of water-repellent material on their surface, are collected on a permeable conveyor 15. The air is allowed to pass through the conveyor and the fibers collected in the form of a lightweight fluffy batt 16 which is water repellent any may be further processed.

Any of the standard hardwood or softwood pulp boards may be used in accordance with the present invention.

By treating wood pulp board in hard, dry sheet form with a water-repellent as it arrives from the pulp mills a number of advantages are achieved. Before the technique described by my present invention, batts of fibers were treated with an additament, such as a water-repellent, after the dry, hard pulp board (received from the pulp mills) was ground or beaten in a wet box. By treating ground fibers with an additament, the fibers became compressed thereby losing the desired and sought after properties of loft, fluffiness and softness. Of course, those treated, compressed fibers could be reconstituted into a board and re-ground, and then air-laid into a fluffy state, but at the extra cost and time of performing the extra operations. Now, with the method of my invention, the extra cost and operations known in the art can be saved by treating the dry, hard wood pulp board before grinding. The result of the grinding and collecting thereafter of the fibers in a batt with the water-repellent material uniformly distributed throughout the batt. This water-repellent batt is fluffy, lofty and soft, and is produced in a minimum amount of cost-saving steps by the critical treatment of hard, dry wood pulp board before grinding.

Suitable water repellents which may be applied to the pulp board are modified cationic thermosetting melamine resins, silicones, waxes, long chain pyridinium compounds, stearate chromium complexes and the like. The repellents may be applied in various solutions or emulsions and are generally applied by spraying though other techniques such as coating may also be used. Depending upon the carrier for the repellent the board may require drying to remove the carrier for the repellent although in some instances when light coatings of high concentrations of repellent are used the drying step may be eliminated.

The treated pulp board is ground to comminute the board and form individualized fibers by and of the standard grinding apparatus such as counter-rotating toothed rolls, Bauer mills, Fitz mills, Hammer mills and the like.

The individual fibers are collected on a conveyor or screen in the form of a lofty batt and the loft and density of the batt may vary to a wide degree dependent upon the speed of grinding, speed of conveying, etc.

In FIG. 2 there is shown a perspective view of a water-repellent, lightweight, lofty batt 20 of wood pulp fibers made in accordance with the present invention. The batt comprises wood pulp fibers 21 and uniformly distributed throughout the wood pulp fibers and the thickness of the batt is water-repellent material 22.

The lofty water-repellent batts of the present invention will contain from about ¼ to 2% by weight of water-repellent material and preferably from about ½% to 1% by weight. The final batts will have a density of from about 0.03 grams per cubic centimeter to 0.30 grams per cubic centimeter and preferably from 0.06 to 0.08 grams per cubic centimeter. The thickness of the final batts range from 1 millimeter to 100 millimeters, and the weight from about 300 grams per square yard to about 600 grams per square yard. The water repellent batts will generally be used in combination with nonwoven fabrics, absorbent media, creped tissue and the like to produce the desired final product.

Having thus generally described the invention reference will be made to the accompanying example which illustrates a preferred embodiment only.

EXAMPLE

A hardwood pulp board in the form of a highly pressed board about five inches wide and ⅛ inch thick is sprayed on one surface with a water-repellent composition. The composition comprises 1.5% by liquid volume of a stearate chromium complex in an isopropanol-water mixture. The board is sprayed to allow the repellent to penetrate the board to about 50% of its thickness. The treated board is ground in a Fitz mill to individualize the fibers and the individualized fibers collected on a screen in the form of a lightweight fluffy batt of fibers having uniformly distributed throughout the thickness of the batt the water repellent material. The resultant batt contains about ½% by weight of water-repellent material and the batt has a density of 0.1 grams per cubic centimeter. The batt is lofty, soft to the hand and readily repels water.

It will be understood that various modifications can be made to the above embodiments without departing from the spirit and scope of this invention.

What is claimed is:

1. A method of manufacturing a water-repellent, fluffy, lightweight batt of wood pulp fibers comprising: providing a prepared hard, substantially dry board of compacted wood pulp fibers, applying to a surface of said board while in a non-aqueous condition between ¼ and 2% by weight of said board of a water-repellent material, said water-repellent coating the fibers of the surface and extending through between 45 and 95% of the depth of the pulp board, grinding the treated pulp board to individualize and uniformly disperse water-repellent treated fibers and untreated fibers, and collecting the individualized fibers in the form of a lofty, fluffy batt of wood pulp fibers having water repellent material uniformly distributed throughout the batt whereby the entire batt is water repellent.

2. A method according to claim 1 wherein the water-repellent material is sprayed on the surface of the pulp board.

3. A method according the claim 1 wherein the pulp board after having a water-repellent material thereon is dried prior to grinding

* * * * *